(12) United States Patent
Bandyopadhyay et al.

(10) Patent No.: US 7,615,574 B2
(45) Date of Patent: *Nov. 10, 2009

(54) SYNERGISTIC COMPOSITION FOR TREATING LEUKEMIA

(75) Inventors: Santu Bandyopadhyay, Kolkata (IN); Bikash Chandra Pal, Kolkata (IN); Samir Bhattacharya, Kolkata (IN); Keshab Chandra Roy, Kolkata (IN); Gautam Bandyopadhyay, Kolkata (IN)

(73) Assignee: Council of Scientific and Industrial Research, New Delhi (IN)

( * ) Notice: Subject to any disclaimer, the term of this patent is extended or adjusted under 35 U.S.C. 154(b) by 425 days.

This patent is subject to a terminal disclaimer.

(21) Appl. No.: 10/613,122

(22) Filed: Jul. 7, 2003

(65) Prior Publication Data

US 2004/0052874 A1   Mar. 18, 2004

Related U.S. Application Data

(60) Provisional application No. 60/393,750, filed on Jul. 8, 2002.

(51) Int. Cl.
*A01N 37/10* (2006.01)
*A61K 31/235* (2006.01)

(52) U.S. Cl. ............................ 514/532; 514/908
(58) Field of Classification Search .............. None
See application file for complete search history.

(56) References Cited

U.S. PATENT DOCUMENTS

| 5,389,371 | A | 2/1995 | Shiao | 424/195.1 |
| 5,582,822 | A | 12/1996 | Brandely et al. | 424/85.2 |
| 6,610,332 | B2 | 8/2003 | Pal et al. | 424/769 |

FOREIGN PATENT DOCUMENTS

| JP | 401261403 A | 10/1989 |
| JP | 09278666 A | 10/1997 |
| JP | 10077495 A | 3/1998 |
| JP | 11130685 A | 5/1999 |

OTHER PUBLICATIONS

Dunussi-Joannopoulos et al. (See Attached Copy).*
Ferguson (Mutation Research/Fundamental and Molecular Mechanisms of Mutagenesis; vol. 475, Issues 1-2, Apr. 18, 2001, pp. 89-111).*
Kuroda et al. (Mutation Research/Reviews in Mutation Research vol. 436, Issue 1, Jan. 1999, pp. 69-97).*
Yang et al. (Drug Metabolism Reviews, vol. 33, Issue 3 & 4 Dec. 2001, pp. 237-253).*
Wealth of India, vol. 8, pp. 84-95.
Sengupta et al., Indian Journal of Experimental Biology (Apr. 2000), vol. 38, 338-342.
Sadasivan et al., Mutation Research, Chromosome-Damaging Effect of Betel Leaf, (1978), vol. 57, pp. 183-185.
Van De Graaff et al., Concepts of Human Anatomy and Physiology, WCB Publishers, (1986) pp. 159, 618, 706-709.
Database WPI, Section CH, Week 199930, Derwent Publications LTD., London, BG; Class B04, an 1999-352797, XP002174279 (JP 11 130685 A).
Database WPI, Section CH, Week 199702, Derwent Publications Ltd., London, BG; Class B04, AN 1997-017312, XP002174280 (JP 08 283171 A).
Mori H et al., "Carcinogenicity Examination of Betel Nuts and Piper Betel Leaves", Experientia (1979), vol. 35, No. 3, pp. 384-385. ISSN: 0014-4754, XP001008625.
Sawyers CL., The New England Journal of Medicine, 340 (17): 1330-1340, 1999.
Vitale C, Romagnani C et al. Proc. Natl. Acd. Sci. USA, 96 (26): 15091-15096.
Vitale C et al., Proc. Natl. Acd. Sci. USA, 98 (10): 5764-5769, 2001.
Sievers El, Appelbaum FR et al. Blood, 93: 3678-3684, 1999.
Ito H et al., Bioorg. Med. Chem. 6(7): 1051-1056, 1998.
Tiyu G, Ftir, Vibrational Spectroscopy, vol. 24, No. 2, 225-231, 2000.
Fung VA, Mutation Research, vol. 204, No. 2, 219-228, 1988.
Y. Kuroda, Bio-antimutagenic acitivty of green tea catechins in cultured Chinese hamster V79 cells, Mutation Research, 361 pgs. 179-186 (1996).
A. Komori et al., "Anticarcinogenic Activity of Green Tea Polyphenols", JPN, J Clin Oncol 23(3), pp. 186-190, (1993).

* cited by examiner

*Primary Examiner*—Sreeni Padmanabhan
*Assistant Examiner*—Layla Soroush
(74) *Attorney, Agent, or Firm*—Fitzpatrick, Cella, Harper & Scinto (57) ABSTRACT

The present invention provides a method of treating acute and chronic myeloid leukemia (AML & CML) and lymphoid leukemia, said method comprising administering a pharmaceutical composition comprising pharmaceutically effective amount of chlorogenic acid (CA) and 3-o-p-Coumaryl quinic acid (PCQ) isolated from any plant parts of *Piper betel* or any other source, both individually or in a synergistic combination optionally along with pharmaceutically acceptable additives.

10 Claims, 5 Drawing Sheets

SYNERGISTIC COMPOSITION FOR TREATING LEUKEMIA

This application claims benefit of U.S. Provisional Application No. 60/393,750 filed Jul. 8, 2002

FIELD OF THE INVENTION

The present invention provides a method of treating acute and chronic myeloid leukemia (AML & CML) and lymphoid leukemia, said method comprising administering a pharmaceutical composition comprising pharmaceutically effective amount of chlorogenic acid (CA) and 3-o-p-Coumaryl quinic acid (PCQ) isolated from any plant parts of *Piper betel* or any other source, both individually or in a synergistic combination optionally along with pharmaceutically acceptable additives.

BACKGROUND AND PRIOR ART REFERENCES

Myeloid leukemia is usually subdivided into two groups: Acute Myeloid Leukemia (AML) and Chronic Myeloid Leukemia (CML). AML is characterized by an increase in the number of myeloid cells in the bone marrow and an arrest in their maturation. In the United States, the annual incidence of AML is approximately 2.4 per 100,000 and it increases progressively with age, to a peak of 12.6 per 100,000 adults 65 years of age or older. The CML is a malignant clonal disorder of hematopoietic stem cells. The median age at presentation is 53 years, but it occurs at all age groups, including children. The natural history of CML is progression from a benign chronic phase to a rapidly fatal blast crisis within three to five years or even earlier. The prognosis of CML is also poor in spite of vast advancement of clinical medicine (1). CD33 represents a specific and useful marker in the process of myeloid cell differentiation (2). Recent reports suggest that engagement of CD33 by monoclonal antibody induced apoptosis leading to growth inhibition of proliferation of AML and CML cells in vitro (2,3). Exploiting the myeloid specific expression of CD33, humanized anti-CD33 monoclonal antibody conjugated with anti-cancer drug has been tried in AML patients with significant success (4). Similarly, lymphoid leukemia is also subdivided in two groups: acute lymphocytic leukemia (ALL) and chronic lymphocytic leukemia (CLL). Lymphoid leukemia may affect both T and B cell lineages and are prevalent in children. With the extracts from *Piper betel* leaves anti-myeloid activity was claimed earlier (Patent filed no. PCT/INOO/00118 dated Dec. 12, 2000) and 3-o-p-Coumaryl quinic acid, an active factor for the treatment of AML and CML on 30.05.2002 U.S. provisional patent Application No. 60/384,163 (299/NF/2002.)

Hence, applicant's earlier findings are in direct consonance with the present patent filing on Chlorogenic acid (CA) isolated from the fractions of the betel leaf extracts for treating acute and chronic myeloid leukemia and lymphoid leukemia. Chlorogenic acid is known to have anti-allergic activity (5). CA also inhibits hepatic and renal glucose-6-phosphatase systems (6). CA is an inhibitor of epidermal lypoxygenase activity and TPA-induced ear inflammation (7). CA also renders inhibitory effects on TPA-induced tumor promotion in mouse skin (7). Anti-HIV activity of CA has also been reported (8). Although inhibition of tumor promotion has been attributed to CA, no anti-tumor activity on established tumors including anti-leukemic activity has not been reported for CA. In the present patent application, anti-leukemic activity and the anti-tumor activity of CA are claimed for the first time.

*Piper betel* leaves have a strong pungent aromatic flavour and are widely used in India as a masticatory. Generally, mature or over mature leaves, which have ceased growing but not yet become brittle are used for chewing. The basic preparation for chewing purposes consists of betel leaf smeared with hydrated lime and catechu to which scrapings of arecanut are added; flavorings such as coconut shavings, clove, cardamom, fennel, powdered liquorice, nutmeg and also tobacco are used according to one's taste. In some places prepared *Piper betel* leaf preparation is covered with silver or gold film. As a masticatory, it is credited with many properties: it is aromatic, digestive, stimulant and carminative. Medicinally it is useful in catarrhal and pulmonary infections; it is also used for poultices. The effects of chewing of betel leaves with arecanut and other adjuncts are the excitation of the salivary glands and the irritation of the mucous membrane of the mouth. The red coloration produced is due to a pigment in the arecanut, which manifests itself under the action of alkali in lime and catechu. A mild degree of stimulation is produced, resulting in a sensation of warmth and well being, besides imparting a pleasant odour. The most important factor determining the aromatic value of the leaf is the amount and particularly the nature of the essential oil present. Betel leaves from different regions vary in smell and taste. The most pungent is the Sanchi type, while the most mild and sweet ones are from Varanasi.

The betal leaves contain essential oils, the content of oil varies from 0.7 to 2.6 per cent depending upon the varieties of leaves. The oil consists of phenols and terpens. The higher the proportion of phenol oil, the better the quality. An isomer of eugenol named chavibetol (betel phenol; 4-alkyl-2-hydroxy-1methoxy benzene) is considered to be characteristic constituent of betel oil. Betel oil of Indian types contains as a predominant phenolic constituent and used in the treatment of various respiratory problems, either as a local application or by gargle. It has carminative properties. It exhibits in different actions on the central nervous system of mammals. The essential oil and extracts of the leaves possess activity against several Gram-positive and Gram-negative bacteria such as *Micrococcus pyogenzes* var. Albus, *Bacillus subtilis* and *B. Megaterium*, *Diplococcus pneumoniae*, *Streptococcus pyogenes*, *Escherichia coli*, *Salmonella typhosa*, *Vibrio comma*, *Shigella dysenteriae*, *Proteus vulgaris*, *Pdseudomonas solanacaerum*, *Sarcina lutea* and *Erwinia carotorora*. The essential oil and leaf extracts also showed anti-fungal activity against *Asperigillus niger* and *A. Oryzae*, *Curvularia lunata* and *Fusarium oxysporum*. The oil is found to be lethal in about 5 minutes to the protozoa, *Paramaeceum caudatum* (5). Steam-distillate of the leaves showed activity against *Mycobacterium tyberculosis*.

REFERENCES

1. Sawyers C L, The New England Journal of Medicine, 340 (17): 1330-1340, 1999.
2. Vitale, C; Romagnani, C, et al., Proc. Natl. Acd. Sci. USA, 96 (26): 15091-15096, 1999.
3. Vitale, C et al., Proc. Natl. Acd. Sci, USA., 98 (10): 5764-5769, 2001.
4. Sievers E L, Appelbaum, F R et al., Blood, 93: 3678-3684, 1999.
5. Ito H, Miyazaki T, Ono M and Sakurai H. Bioorg. Med. Chem. 6(7): 1051-1056, 1998.
6. Arion W J et. al. Arch. Biochem. Biophys. 351(2): 279-285, 1998.

7. Conney A H et.al. Adv. Enzyme Regul. 31: 385-396, 1991.
8. Supriyatna G et.al. Phytomedicine, 7 (Suppl. II): 87, 2000.

OBJECT OF THE INVENTION

The main object of the present invention is to identify an synergy in the compounds CA and PCQ in the management of leukemia.

Another objective of the invention is to provide a new use of the compound Chlorogenic acid isolated from the *Piper betel* leaf extract or from any other sources for the treatment of acute and chronic myeloid leukemia and lymphoid leukemia.

Another objective of the invention is to provide a new pharmaceutical composition comprising a carrier along with the compound Chlorogenic acid for the treatment of acute and chronic myeloid leukemia and lymphoid leukemia.

Yet another objective of the invention is to provide a process for the isolation of an active fraction from leaves or any other plant parts of *Piper betel* to treat AML, CML and lymphoid leukemia.

Yet another objective of the invention is to provide a simplified method of isolation of active components from all plant parts of *Piper betel* possessing biological activities relevant to the treatment of AML, CML and lymphoid leukemia.

Yet another objective of the invention is to provide a herbal product from leaves or any other plant parts of *Piper betel* for the treatment of AML, CML and lymphoid leukemia.

Yet another objective of the invention is to provide a herbal Chlorogenic acid purified from leaves of *Piper betel* for the treatment of AML, CML and lymphoid leukemia.

Yet another objective of the invention is to provide a process for the preparation of extract from leaves or any other plant parts of *Piper betel* for the treatment of AML, CML and lymphoid leukemia.

Yet another objective of the invention is to provide a simplified method of extract preparation from leaves or any other plant parts of *Piper betel* for the treatment of AML, CML and lymphoid leukemia.

Yet another objective of the invention is to provide a process for the preparation of Chlorogenic acid from leaves of *Piper betel* for the treatment of AML, CML and lymphoid leukemia.

Yet another objective of the invention is to provide herbal Chlorogenic acid purified from leaves or any other plant parts of *Piper betel* for the treatment of solid tumors including lymphomas.

Yet another objective of the invention is to provide new uses of Chlorogenic acid (isolated from any source or synthetically prepared) for the treatment of acute and chronic myeloid leukemia, lymphoid leukemia and solid tumors including lymphomas.

SUMMARY OF THE INVENTION

Accordingly, the present invention provides a method of treating acute and chronic myeloid leukemia (AML & CML) and lymphoid leukemia, said method comprising administering a pharmaceutical composition comprising pharmaceutically effective amount of chlorogenic acid (CA) and 3-o-p-Coumaryl quinic acid (PCQ) isolated from any plant parts of *Piper betel* or any other source, both individually or in a synergistic combination optionally along with pharmaceutically acceptable additives.

DETAILED DESCRIPTION OF THE INVENTION

Figure 3:
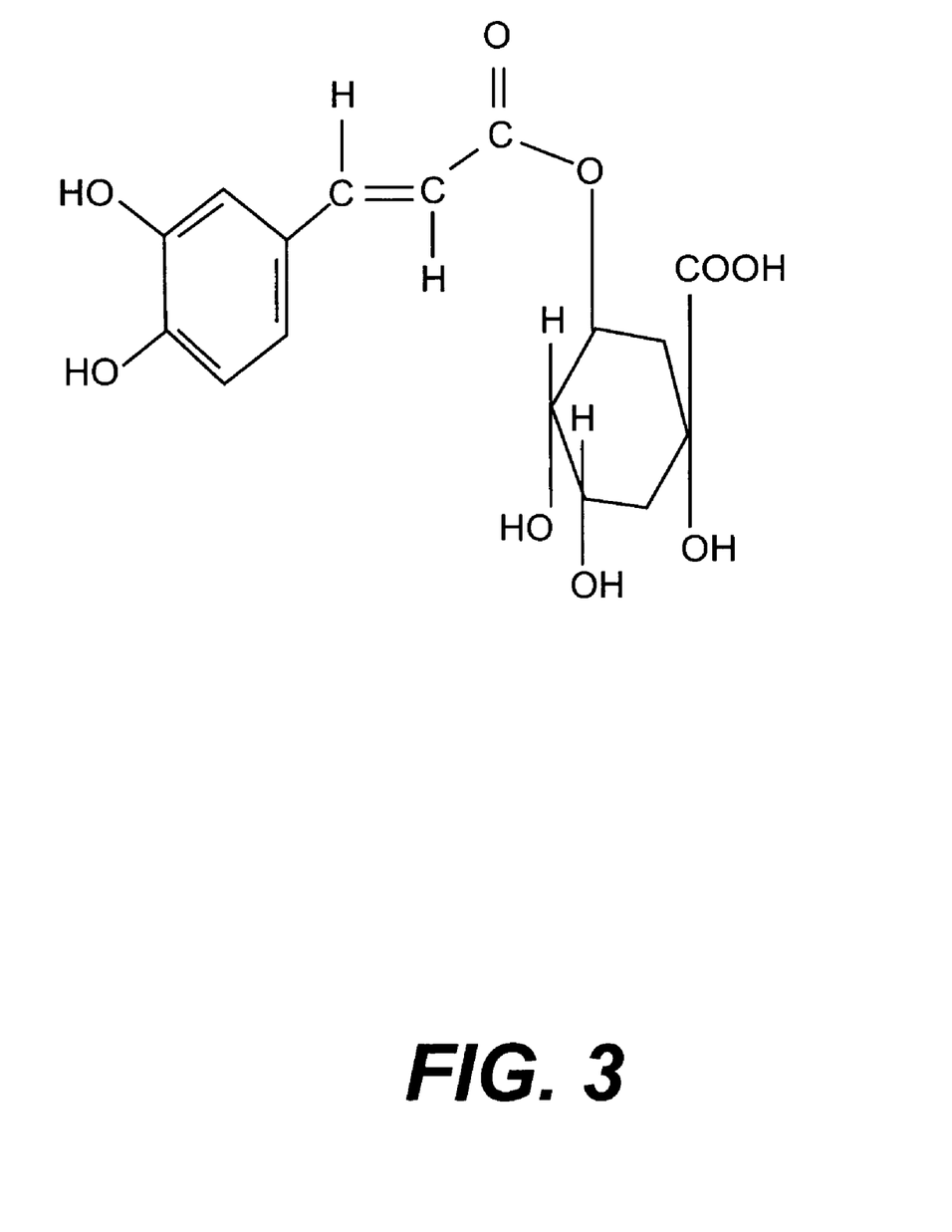
FIG. 3 represents the structure of Chlorogenic acid (CA) or 3-Caffeoyl quinic acid.
Figure 4:
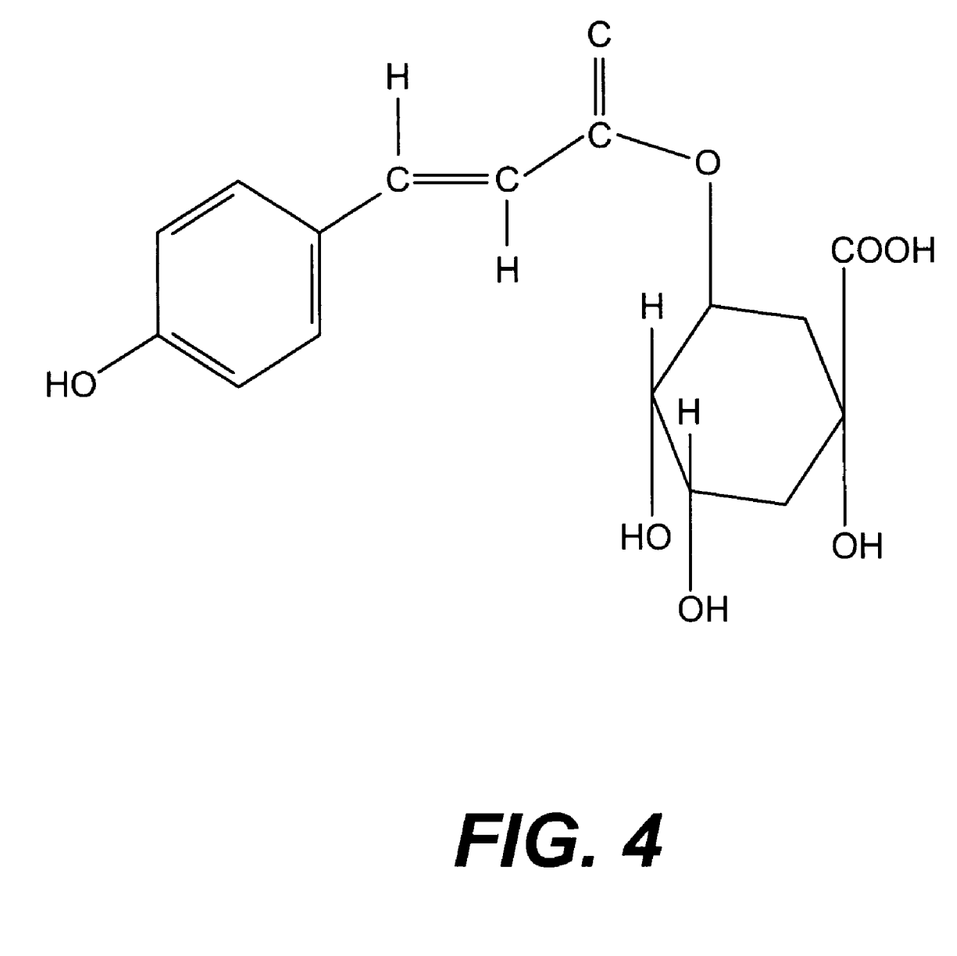
FIG. 4 represents structure of 3-O-p-coumaryl quinic acid [PCQ].

In accordance, the present invention provides a method of treating acute and chronic myeloid leukemia (AML & CML) and lymphoid leukemia, said method comprising administering a pharmaceutical composition comprising pharmaceutically effective amount of chlorogenic acid (CA) [FIG. 3] and 3-o-p-Coumaryl quinic acid (PCQ) [FIG. 4] isolated from any plant parts of *Piper betel* or any other source, both individually or in a synergistic combination optionally along with pharmaceutically acceptable additives.

Yet another embodiment of the present invention, CA and PCQ both are isolated from any plant parts of *Piper betel* or are synthetically prepared. Still another embodiment of the present invention, the subject is selected from a mammal preferably a human being.

Yet another embodiment of the present invention, the additive is selected from a group consisting of nutrients such as proteins, carbohydrates, sugars, talc, magnesium stearate, cellulose, calcium carbonate, starch-gelatin paste and/or pharmaceutically acceptable carriers, excipient, diluents or solvents.

Still another embodiment of the present invention, ratio of CA and PCQ present in the composition ranging from 1:0 to 1:10, is effective for the treatment of solid tumors including lymphomas.

Yet another embodiment of the present invention, the said composition is administered through oral, intravenous, intramuscular or subcutaneous routes.

Still another embodiment of the present invention, said composition is administered at dose levels between 1 to 50 mg per kg body weight at least once in a day.

Yet another embodiment of the present invention, the percentage growth inhibition of Erythroleukemia cells is about 30% with CA.

Still another embodiment of the present invention, the percentage growth inhibition of Erythroleukemia cells is about 8% with PCQ.

Yet another embodiment of the present invention, the percentage growth inhibition of Erythroleukemia cells is about 50% with CA and PCQ as synergistic combination.

Still another embodiment of the present invention, wherein the percentage growth inhibition of promonocyte cells is about 25% with CA.

Yet another embodiment of the present invention, the percentage growth inhibition of promonocyte cells is about 5% with PCQ.

Still another embodiment of the present invention, the percentage growth inhibition of promonocyte cells is about 55% with CA and PCQ as synergistic combination.

Yet another embodiment of the present invention, wherein the percentage growth inhibition of CML's leukemic cells is about 5% with CA.

Still another embodiment of the present invention, wherein the percentage growth inhibition of CML's leukemic cells is about 5% with PCQ.

Yet another embodiment of the present invention, the percentage growth inhibition of CML's leukemic cells is about 25% with CA and PCQ as synergistic combination.

Still another embodiment of the present invention, the percentage inhibition of leukemic cells with increase in the time duration of exposure to CA and PCQ both individually in synergistic combination.

This invention relates to treatment of acute and chronic myeloid leukemia (AML and CML) and also of lymphoid leukemia by Chlorogenic acid (CA) isolated from *Piper betel* leaf extract. Myeloid leukemia, both acute (AML) and chronic (CML) and lymphoid leukemia are lethal, there is no drug directing towards the destruction of the leukemic cells, and these cells poorly respond to chemotherapy which is always non-specific thus adversely affecting normal cells. Unique property of the therapy with *Piper betel* component (Chlorogenic acid) is the killing of myeloid cancer cells and lymphoid cancer cells leaving other normal cells unaffected.

Accordingly, the present invention provides a new use of the compound chlorogenic acid isolated from the piper betel leaf extract or from any other sources for the treatment of acute and chronic myeloid leukemia and lymphoid leukemia. In addition the present invention provides a pharmaceutical composition for acute and chronic myeloid leukemia in animals and humans, said composition comprising effective amount of chlorogenic acid (CA) and/or 3-o-p-Coumaryl quinic acid (PCQ), isolated from any plant parts of *Piper betel* or any other natural or synthetic source and pharmaceutical acceptable additives.

In accordance, the present invention provides a pharmaceutical composition for acute and chronic myeloid leukemia in animals and humans, said composition comprising effective amount of chlorogenic acid (CA) and/or 3-o-p-Coumaryl quinic acid (PCQ), isolated from any plant parts of *Piper betel* or any other natural or synthetic source and pharmaceutical acceptable additives.

One embodiment of the invention, the additive is selected from a group consisting of nutrients such as proteins, carbohydrates, sugars, talc, magnesium stearate, cellulose, calcium carbonate, starch-gelatin paste and/or pharmaceutically acceptable carriers, excipient, diluents or solvents.

Another embodiment, ratio of CA and PCQ present in the composition ranging from 1:0 to 1:10, which is effective for the treatment of solid tumors including lymphomas.

Still another embodiment, the said composition is administered through oral, intravenous, intramuscular or subcutaneous routes.

Yet another embodiment, the composition is administered at a dose level ranging between 1 and 50 mg per kg body weight/day for at least for a period of four weeks.

Yet another embodiment, the composition is administered for a period ranging between four weeks and twelve weeks.

In yet another embodiment, the growth inhibition of leukemic cell lines $2 \times 10^6$/ml/well of cell type K562 is up to 20% at a dose level of 25 µg/ml of CA.

In yet another embodiment, the growth inhibition of leukemic cell lines $2 \times 10^6$/ml/well of cell type K562 is up to 4% at a dose level of 25 µg/ml of PCQ.

In yet another embodiment, the growth inhibition of leukemic cell lines $2 \times 10^6$/ml/well of cell type K562 is up to 44% at a dose level containing 25 µg/ml each of CA and PCQ.

In yet another embodiment, the growth inhibition of leukemic cell lines $2 \times 10^6$/ml/well of cell type U937 is up to 16.67 at a dose level of 25 µg/ml of CA.

In yet another embodiment, the growth inhibition of leukemic cell lines $2 \times 10^6$/ml/well of cell type U937 is up to 2.08% at a dose level of 25 µg/ml of PCQ.

In yet another embodiment, the growth inhibition of leukemic cell lines $2 \times 10^6$/ml/well of cell type U937 is up to 50% at a dose level containing 25 µg/ml each of CA and PCQ.

In yet another embodiment, the growth inhibition of leukemic cell lines $2 \times 10^6$/ml/well of cell CML leukemic cells is up to 2.38 at a dose level of 25 µg/ml of CA.

In yet another embodiment, the growth inhibition of leukemic cell lines $2 \times 10^6$/ml/well of CML leukemic cells is up to 2.38% at a dose level of 25 µg/ml of PCQ.

In yet another embodiment, the growth inhibition of leukemic cell lines $2 \times 10^6$/ml/well of CML leukemic cells is up to 20.3% at a dose level containing 25 µg/ml each of CA and PCQ.

One more embodiment provides the use of composition for the treatment of acute and chronic myeloid leukemia (AML & CML) and lymphoid leukemia by administering a pharmaceutical composition comprising effective amount of chlorogenic acid (CA) and/or 3-o-p-Coumaryl quinic acid (PCQ), isolated from any plant parts of *Piper betel* or any other source and/or in combination with pharmaceutically acceptable additives.

Yet another object of the invention is to provide a herbal compound 3-O-p-coumaryl quinic acid purified from leaves of *Piper betel* for the treatment of CD33+ AML and CML.

Yet another object of the invention is to provide a process for the preparation of 3-O-p-coumaryl quinic acid from leaves of *Piper betel* for the treatment of CD33+ AML and CML.

Yet another object of the invention is to provide a simplified method of preparation of 3-O-p-coumaryl quinic acid from all plant parts of *Piper betel* for the treatment of CD33+ AML and CML.

Yet another embodiment of the present invention, treating CD33+ both acute and chronic myeloid leukemia in mammals including humans, using compound 3-O-p-coumaryl quinic acid obtained from the fraction 9 of polar extract of *piper betel* by HPLC, with retention time of about 24.0 minutes, said method comprising steps of administering the fraction(s) intravenously to a patient of myeloid leukemia.

Another embodiment of the present invention, the compound 3-O-p-coumaryl quinic acid shows 100% efficacy against acute myeloid leukemia at concentration of about 600 µg/ml.

Still another embodiment of the present invention, compound 3-O-p-coumaryl quinic acid shows about 85% efficacy against chronic myeloid leukemia at concentration of about 600 µg/ml.

Another embodiment of the present invention, compound 3-O-p-coumaryl quinic acid shows about 60% efficacy against acute myeloid leukemia at concentration of about 100 µg/ml.

Yet embodiment of the present invention, concentration of compound 3-O-p-coumaryl quinic acid is ranging between 50-700 µg/ml.

The invention is described herein below with reference to examples, which are illustrative only and should not be construed to limit the scope of the present invention in any manner.

EXAMPLE 1

Collection of Plant Material

The leaves and all other plant parts of *Piper betel* were collected from the climber from different areas and West Bengal, India. A voucher specimen was deposited at the Deptt. of Medicinal Chemistry at the Indian Inst. of Chemical Biology, 4 Raja S.C. Mullick Road, Kolkata-700 032.

EXAMPLE 2

Isolation of Compound Chlorogenic Acid 4.7 Kg of *Piper betel* leaves freshly collected, washed with distilled water and then cut into small pieces. Small pieces of leaves were gathered together, mixed with 1.0 litre of distilled water, and thoroughly homogenized in a mixture blender. The homogenate was passed through a fine cheesecloth to filter out the large particles and the filtrate was collected. The process was repeated 2-3 times to have maximum yield. The combined filtrate was then centrifuged, the aliquot, a clear solution, was collected and lyophilised to a semi-solid mass, which was about 110 gm.

Figure 1:
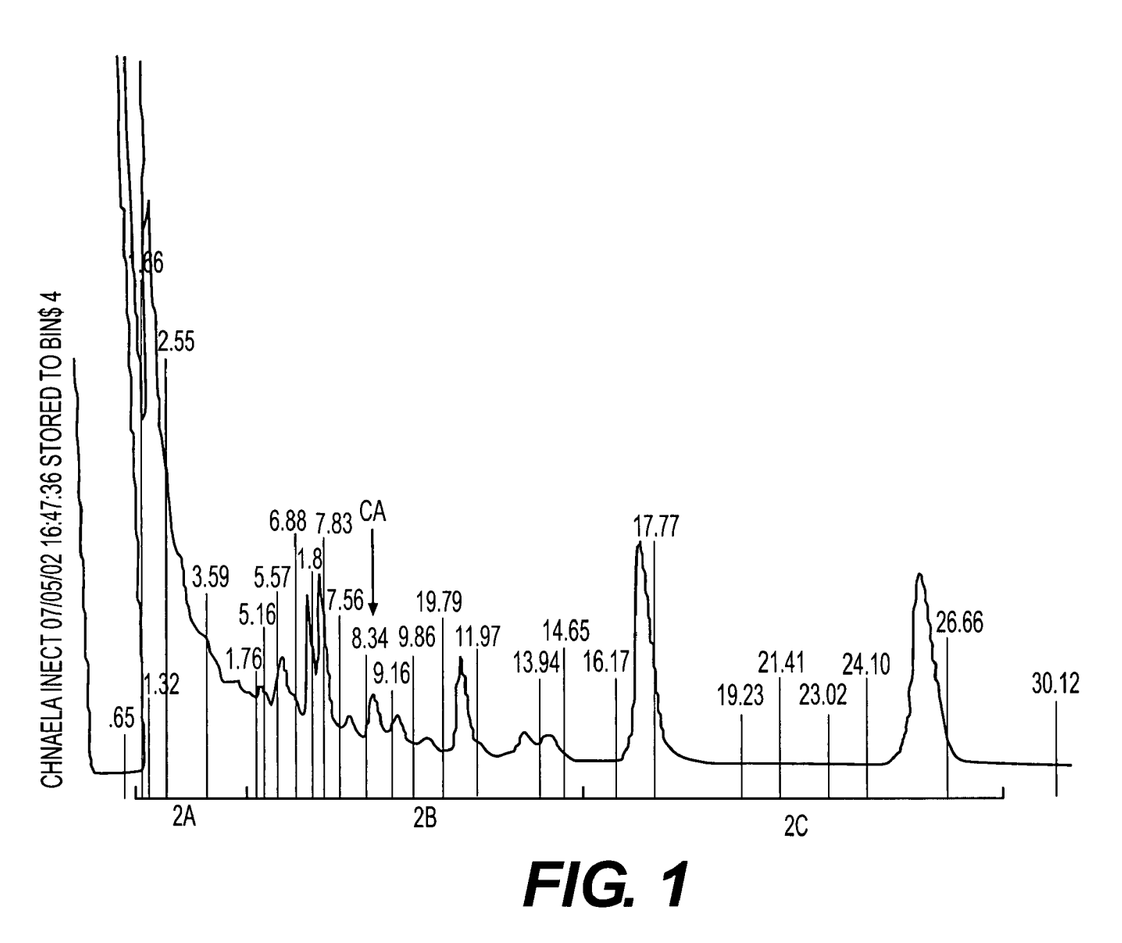
FIG. 1 represents HPLC of Fraction E showing the retention time (RE) of different peaks be divided into three zones, $Z_A$, $Z_B$ and $Z_C$.

Collected material was examined for biological activity i.e. destruction of leukemic cells. On observing its positive activity, purification was initiated. 10 gm of above-mentioned material was loaded on Sephadex LH-20 column and chromatographed with water, water-methanol (1:1) and methanol as eluent. Three different fractions thus obtained from three different solvent systems were separately checked for biological activity. The activity was located only on Fraction 2 i.e. Methanol-water (1:1) and termed as fraction E. Fraction E was then subjected to HPLC analysis using Intersil ODS-3 analytical column. The column was equilibrated with methanol-water-acetic acid (23:76:1), flow rate was maintained at 1.0 ml per min and peaks were identified at 280 nm. According to the retention time (RE) different peaks could be divided into three zones, $Z_A$, $Z_B$ and $Z_C$ (FIG. 1). $Z_A$ had 4 major peaks whereas $Z_B$ had very small to moderate 10 peaks and $Z_C$ had two distinct peaks. It was convenient to observe biological activity of three zones $A_A$, $Z_B$ and $Z_C$, which were separately tested on leukemia cells for destructive activity. All three showed biological activity.

It may be noted here that $Z_C$ which had two distinct peaks with retention time $(R_t)$ 17.77 and 26.66 min. $R_t$ 17.77 min peak demonstrated considerable activity and therefore its structure was determined and filed for patent (299/NF/2002; dated-30.05.2002). The latter i.e. $R_t$ 26.66 min peak did not show any activity.

Figure 2:
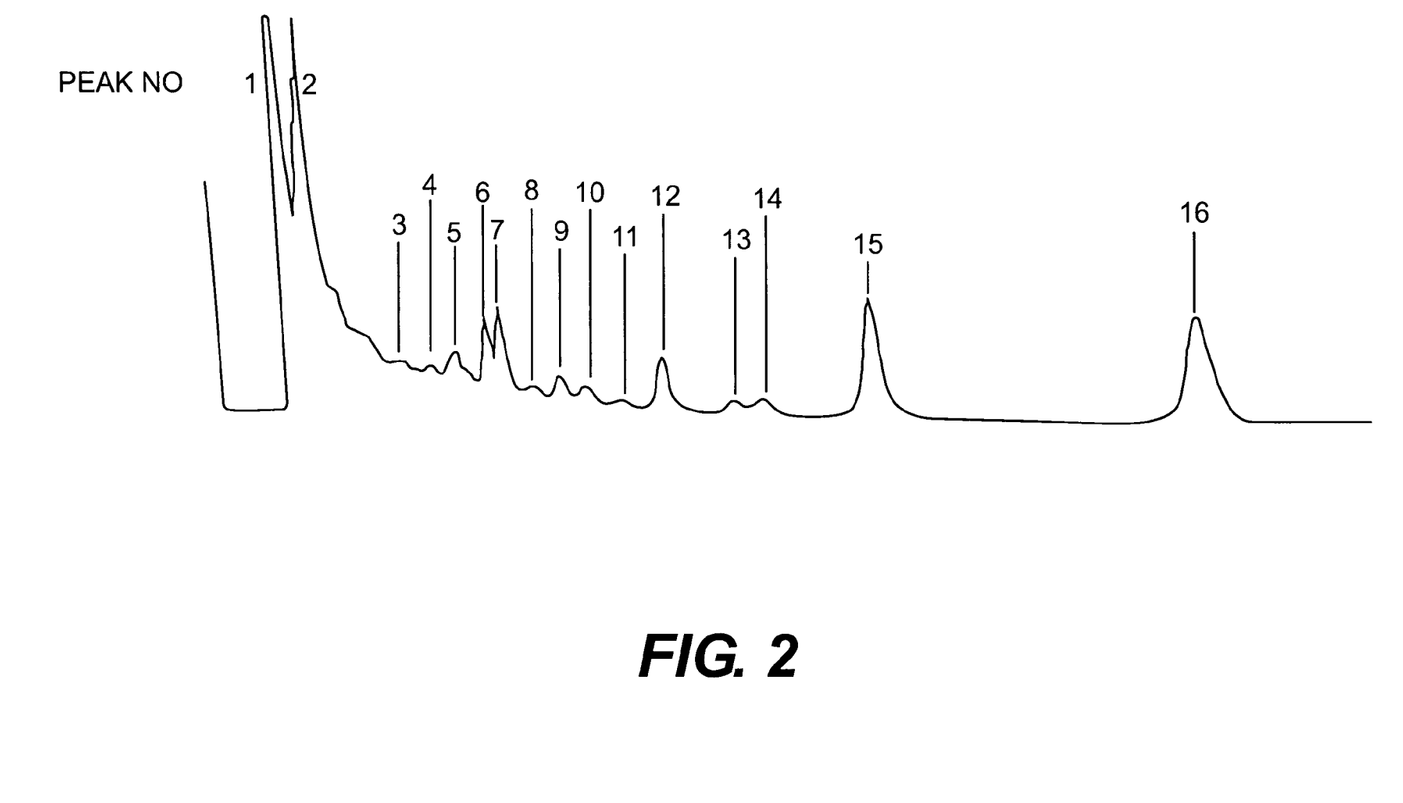
FIG. 2 The peaks have been numbered ($Z_A$ had 4 major peaks whereas $Z_B$ had very small to moderate 10 peaks and $Z_C$ had two distinct peaks).

The Zone $Z_B$ contained 10 peaks (1 to 10) of varied sizes. Pooled 1-10 peaks fraction demonstrated leukemic cell killing activity. For this reason all different peaks were separately monitored for biological activity. Major peaks amongst them were 2,3,4 and 8 corresponding to $R_t$ 6.58, 7.14, 7.56 and 11.97 respectively and none of them exhibited activity. Hence minor peaks were separately examined by collecting repeated fractions for each peaks to increase the amount of active molecules present there. On searching for activity of these peaks i.e. 1,5,6,7,9 and 10 corresponding to $R_t$ 5.16, 8.34, 9.16, 9.86, 13.94 and 14.68 respectively. Except peak no 6 ($R_t$ 9.16 min) no other peaks had shown detectable activity. Peak 6 ($R_t$ 9.16 min) pooled fractions were lyophilized and reran through HPLC, the sharp single peak indicate its purity (FIG. 2). This was then subjected to IR, NMR and Mass spectral analysis to determine the structure.

| KBr | |
|---|---|
| IR γmax cm$^{-1}$: | 3355(OH), 1689(CO), 1637, 1604 1522, 1443, 1286, 1189, 1121, 1082 1039, 975 and 854 |
| $^1$H-NMR (CD$_3$OD): | 7.57(1H), 7.06(1H), 6.96(1H), 6.79(1H) 6.27(1H), 5.34(1H), 4.17(1H), 3.73(1H) and 2.13(4H) |
| $^{13}$C NMR (CD$_3$OD): | 176.00, 167.65, 148.56, 146.08, 145.79, 126.78, 121.98, 115.46, 114.24, 75.11, 72.45, 70.96, 70.26, 37.75 and 37.19 |
| FABMS m/Z: | 355 (M$^+$ + H) and 377 (M$^+$ + Na) |

The structure thus determined shows it to be chlorogenic acid or 3-Caffeoyl quinic acid, m.p. 205°-206° C. $[\alpha]_D$-33.25 (H$_2$O) (FIG. 3). The chlorogenic acid is available in the market in pure form. This was bought and compared with the chlorogenic acid isolated from *Piper betle* leaves, which clearly confirmed that, the available material as chlorogenic acid.

Structure filed for patent earlier was 3-p-coumaryl quinic acid which showed CD33+ myeloid cells destruction but not CD33− cells, and this is very mimilar to chlorogenic acid. Except the additional hydroxyl group at C-3 position of the aromatic ring in chlorogenic acid other structures are precisely similar. Therefore, the additional activity of chlorogenic acid over the 3-p-coumaryl quinic acid can be suggested to be due to the presence of hydroxyl group at C-3 position of aromatic ring. This specific difference has given broader and stronger activity to Chlorogenic acid in destroying both CD33− and CD33+ cells and also lymphoid leukemic cells.

Zone $Z_A$ demonstrated bilogical activity. It contained 4 peaks, 1,2,3 and 4 corresponding to $R_t$ 0.65, 1.32, 1.8 and 2.55 respectively. Since separation of individual peak under $Z_A$ becomes difficult, location of peak wise activity could not be determined.

EXAMPLE 3

Preparation of peripheral blood mononuclear cells (PBMC) from myeloid leukemia patients.

Whole blood (10 ml each) was drawn from previously diagnosed myeloid leukemic patients, one patient was diagnosed as AML and the other one was diagnosed as CML. Mononuclear cells were separated by Ficoll/hypaque density gradient centrifugation.

EXAMPLE 4

Culture of Erythroleukemic cell line K562. This cell line was collected from American Type Culture Collection (ATCC), VA, USA. This cell line is CD33$^−$. K562 cells were grown in vitro in Medium RPMI-1640 containing 10% heat inactivated fetal calf serum.

EXAMPLE 5

Culture of Promonocytic cell line U937. This cell line was obtained from American Type Culture Collection (ATCC), VA, USA, and grown in vitro as described for the cell line K562. This cell line is CD33$^+$.

EXAMPLE 6

Incubation of PBMC of myeloid leukemia patients with Chlorogenic acid (CA) in vitro.

PBMC ($1\times10^5$-$2\times10^6$/ml) of myeloid leukemia patients were incubated with varied concentrations of CA for 48 hours at 37° C. in 5% $CO_2$. Cells were then washed and counted for viability.

EXAMPLE 7

Incubation of $CD33^+$ cell line U937 with CA. U937 cells ($1\times10^5$-$2\times10^6$/ml) were incubated with varying concentrations of CA for 48 hours at 37° C. in 5% $CO_2$. Cells were then washed and counted for viability.

EXAMPLE 8

Incubation of $CD33^-$ cell line K562 with CA. K562 cells ($1\times10^5$-$2\times10^6$/ml) were incubated with varying concentrations of CA for 48 hours at 37° C. in 5% $CO_2$. Cells were then washed and counted for viability.

EXAMPLE 9

Culture of T-Lymphoid cell line Molt-4. This cell line was obtained from American Type culture collection (ATCC), VA, USA and grown in vitro as described for the cell line K562.

EXAMPLE 10

Preparation of peripheral blood mononuclear cells (PBMC) from normal individuals. Whole blood was collected and mononuclear cells were separated by Ficoll/Hypaque density gradient centrifugation.

EXAMPLE 11

Analysis of cell cycle progression and apoptosis by Flow cytometry PBMC of a CML patient was cultured in RPMI-1640 medium supplemented with 10% heat-activated fetal bovine serum in the presence or absence of CA (100.0 μg/ml) for 48 hr. at 37° C. in 5% $CO_2$. Cells were fixed with 40% ethanol treated with 500 μg/ml Rnase A, and then with 69 μM propidium iodide for analysis of DNA content by Flow Cytometry as described (Mitra et al., Molecular Medicine, 6:527-541, 2000).

Results of Examples 6, 7 & 8

As shown in Table 1, PBMC of myeloid leukemia patients, $CD33^+$ Promonocytic cell line U937 and $CD33^-$ Erythroleukemic cell line K562 were destroyed by Chlorogenic acid.

Results of Example 9 and 10

Figure 5:
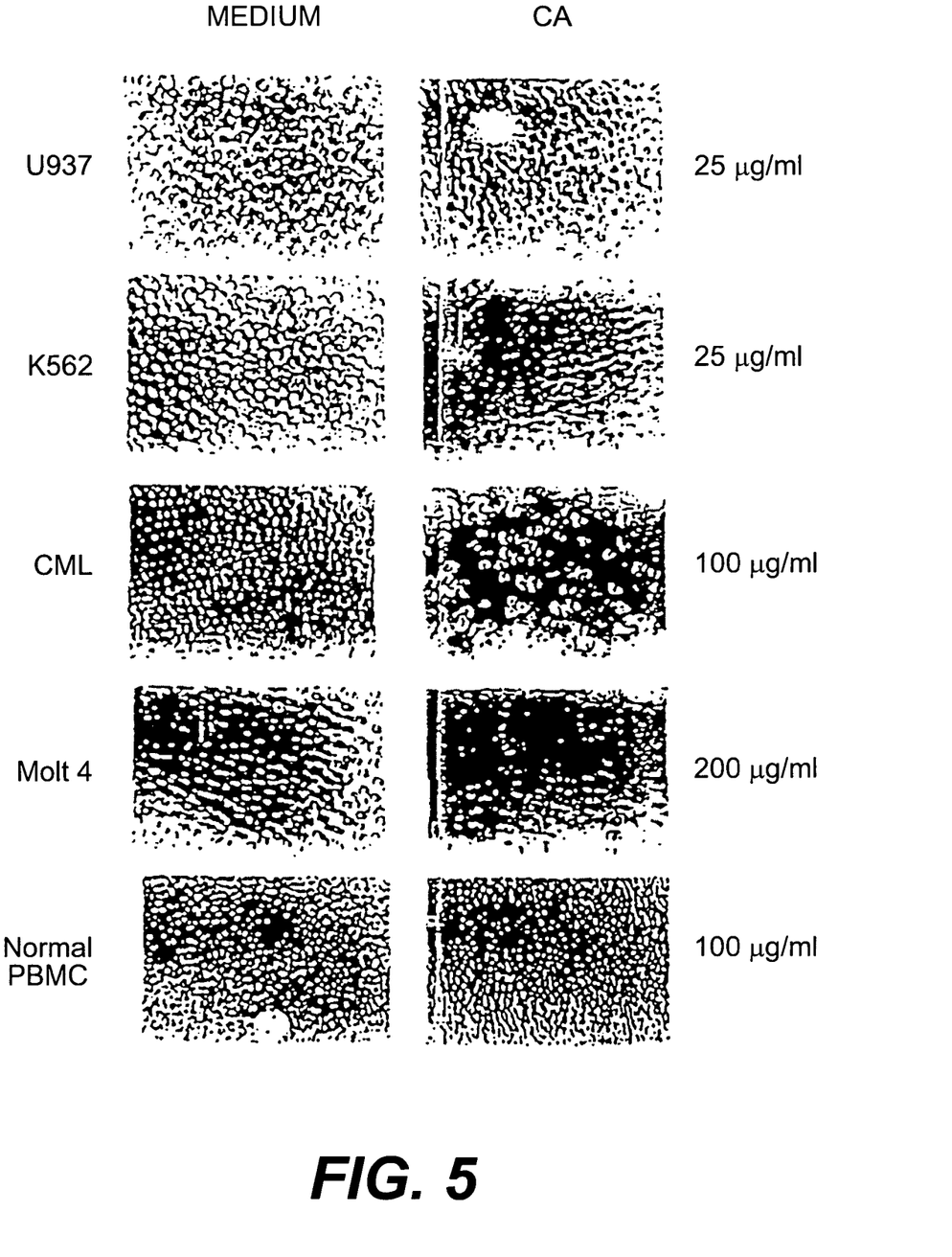
FIG. 5 represents photomicrographs of Leukemic cell lines, CML Patient's and normal donor's PBMC after treatment with CA.

As shown Table 2, Erythroleukemia cell line K562, Promonocyte cell line U937 and CML patient's leukemic cells are destroyed by Chlorogenic acid T-lymphoid cell line Molt-4 requires higher dose. In contrast, PBMC of normal donors are virtually unaffected by CA. Photomicrographs of U937, K562, CML Patient's PBMC, Molt-4 and normal PBMC after culturing for 48 hr. in the presence or absence of CA are shown in FIG. 5. We claimed earlier that 3-o-p-Coumaryl quinic acid (PCQ) has anti myeloid leukemia activity (299/NF/2002; 30.05.2002). Here we show that combination of chlorogenic acid (CA) and 3-o-p-coumaryl quinic acid at a ratio of 1:1 is more effective than CA or PCQ alone in destroying Leukemic cell lines or Myeloid Leukemia patient's Lekemic cells but have no effects on normal donor's PBMC (Table 3).

Results of Example 11

Cell-cycle analysis demonstrate that after two days of culture, chlorogenic acid at a concentration of 100.0 μg/ml caused apoptosis in CML patients Leukemic cells in vitro because of their accumulation in S, $G_2$ or M phase compared to the cells cultured in medium alone (Table 4).

TABLE I

Chlorogenic acid destroys patients' leukemic cells and leukemia cell lines in vitro.

| | Percent inhibition of cell growth after 48 hr of incubation | | | |
|---|---|---|---|---|
| Compound | AML patient's PBMC* | CML patient's PBMC | Promonocytic cell line (U937) | Erythroleukemic cell line (K562) |
| Medium alone | 0.0 | 0.0 | 0.0 | 0.0 |
| Chlorogenic acid (CA) | | | | |
| 10 μg/ml | ND | ND | 25.0 | 46.6 |
| 15 μg/ml | ND | ND | 43.7 | 93.3 |
| 20 μg/ml | 9.5 | 5.8 | 90.6 | 100.0 |
| 50 μg/ml | 16.6 | 10.3 | — | — |
| 100 μg/ml | 73.8 | 22.5 | — | — |
| 500 μg/ml | 85.7 | 32.3 | — | — |

Note:
1. PBMC*, Peripheral blood mononuclear cells.
2. The number of cells used was $1 \times 10^5$/ml/well

TABLE 2

Growth inhibition of Leukemic Cell Lines and CML Patient's Leukemic Cells by CA in vitro.

| | Incubated with | Percentage Inhibition of Cell Growth | | |
|---|---|---|---|---|
| Cells | (μg/ml) | 1 day | 2 days | 3 days |
| K 562 | Medium | 0.00 | 0.00 | 0.00 |
| | CA (10.0) | 8.00 | 48.14 | 85.18 |
| | CA (25.0) | 20.00 | 62.96 | 92.59 |
| | CA (50.0) | 28.00 | 77.78 | 100.0 |
| | CA (100.0) | 84.00 | 98.14 | 100.0 |
| U937 | Medium | 0.00 | 0.00 | 0.00 |
| | CA (10.0) | 8.33 | 44.0 | 57.14 |
| | CA (25.0) | 16.67 | 52.00 | 71.42 |
| | CA (50.0) | 25.00 | 64.00 | 89.28 |
| | CA (100.0) | 45.83 | 96.00 | 100.0 |
| Molt 4 (T lymphoid Cell line) | Medium | 0.00 | 0.00 | 0.00 |
| | CA (50.0) | 3.57 | 6.67 | 12.5 |
| | CA (100.0) | 6.89 | 14.67 | 18.75 |
| | CA (200.0) | 13.79 | 46.67 | 62.5 |
| CML Patient's PMBC | Medium | 0.00 | 4.67 | 14.28 |
| | CA (50.0) | 4.76 | 22.22 | 30.0 |
| | CA (100.0) | 9.52 | 45.0 | 55.56 |
| Normal PBMC | Medium | 0.00 | 3.33 | 3.33 |
| | CA (50.0) | 1.03 | 10.34 | 15.2 |
| | CA (100.0) | 6.66 | 17.24 | 19.5 |

Of note, the number of cells used was $1 \times 10^5$ per ml per well.

TABLE 3

Combination of Chlorogenic Acid (CA) and 3-o-p-Coumaryl
Quinic acid (PCQ) is more effective in destroying
Leukemic cell lines and AML and CML patient's
Leukemic cells in vitro as compared to CA and PCQ individually.

| Cells | Incubated with | % Inhibition of cell growth (After 1 day of incubation) |
|---|---|---|
| K 562 | Media | 0.00 |
| Erythroleukemia | CA (25.0 µg/ml) | 20.00 |
| cell line | CA (50.0 µg/ml) | 28.00 |
|  | PCQ (25.0 µg/ml) | 4.00 |
|  | PCQ (50.0 µg/ml) | 8.00 |
|  | CA (25.0 µg/ml) + PCQ (25.0 µg/ml) | 44.00 (synergistic effect) |
| U937 | Media | 0.00 |
| Promonocyte cell line | CA (25.0 µg/ml) | 16.67 |
|  | CA (50.0 µg/ml) | 25.00 |
|  | PCQ (25.0 µg/ml) | 2.08 |
|  | PCQ (50.0 µg/ml) | 4.17 |
|  | CA (25.0 µg/ml) + PCQ (25.0 µg/ml) | 50.00 (synergistic effect) |
| CML Patient's Leukemic cells | Media | 0.00 |
|  | CA (25.0 µg/ml) | 2.38 |
|  | CA (50.0 µg/ml) | 4.67 |
|  | PCQ (25.0 µg/ml) | 2.38 |
|  | PCQ (50.0 µg/ml) | 4.67 |
|  | CA (25.0 µg/ml) + PCQ (25.0 µg/ml) | 20.3 (synergistic effect) |
| Normal individual's PBMC | Media | 0.00 |
|  | CA (25.0 µg/ml) | 1.03 |
|  | CA (50.0 µg/ml) | 1.03 |
|  | PCQ (25.0 µg/ml) | 0.00 |
|  | PCQ (50.0 µg/ml) | 1.67 |
|  | CA (25.0 µg/ml) + PCQ (25.0 µg/ml) | 1.03 |

The number of cells used was $2 \times 10^6$ per ml per well. The percentage of killing of cells by these compounds is dependent on the number of cells present per ml. Further, the percentage killing was seen to increase with the increase in the time duration of exposure to the synergistic combination. The combination is able to cause percentage inhibitor must faster as compared to the compounds CA or PCQ individually.

The protocols of Table Nos.2 and 3 are distinct. The reaction conditions are totally distinct and this is confirmed by the results.

The combination of CA and PCQ shows synergy. When CA or PCQ are administered independently, the results were ordinary. However, combination of CA and PCQ brought about unexpected results.

The combination of these two compounds showed surprisingly high activity in the management of AML, CML and lymphoid leukemia. The combination of these compounds probably led to a certain action mechanism is facilitated the inhibition of cell growth in leukemic cells. The results were consistent and reproducible.

TABLE 4

The percentage of cells indifferent phases of cell cycle
after treatment with CA for 2 days

| Type of cells | Incubated with | Sub G0/G1 (apoptotic, 2n DNA) | G0/G1 (2n DNA) | S + G2 + M (>2n DNA) |
|---|---|---|---|---|
| CML Patient's leukemic Cells | Media | 4.65 | 51.56 | 43.87 |
|  | CA (100.0 µg/ml) | 10.64 | 33.13 | 56.35 |

We claim:

1. A method of treating acute and chronic myeloid leukemia (AML & CML) and lymphoid leukemia, in a mammal, in order to obtain a percentage growth inhibition of at least one of promonocyte cells, Erythroleukemia cells, or CML's leukemic cells, said method comprising administering a pharmaceutical composition consisting essentially of a pharmaceutically effective amount of chlorogenic acid (CA) and 3-o-p-Coumaryl quinic acid (PCQ) isolated from any plant parts of *Piper betel* or any other source, optionally along with pharmaceutically acceptable additives, wherein the ratio of CA and PCQ in the composition ranges from 1:1 to 1:10.

2. A method as claimed in claim 1, wherein, CA and PCQ both are isolated from any plant parts of *Piper betel* or are synthetically prepared.

3. A method as claimed in claim 1, wherein the selected mammal is a human being.

4. A method as claimed in claim 1, wherein, the additive is selected from a group consisting of nutrients such as proteins, carbohydrates, sugars, talc, magnesium stearate, cellulose, calcium carbonate, starch-gelatin paste and/or pharmaceutically acceptable carriers, excipient, diluents or solvents.

5. A method as claimed in claim 1, wherein the said composition is administered to the mammal through oral, intravenous, intramuscular or subcutaneous routes.

6. A method as claimed in claim 1, wherein said composition is administered to the mammal at dose levels between 1 to 50 mg per body weight at least once in a day.

7. A method as claimed in claim 1, wherein the percentage growth inhibition of Erythroleukemia cells is about 50% with CA and PCQ used in combination.

8. A method as claimed in claim 1, wherein the percentage growth inhibition of promonocyte cells is about 55% with CA and PCQ used in combination.

9. A method as claimed in claim 1, wherein the percentage growth inhibition of CML's leukemic cells is about 25% with CA and PCQ used in combination.

10. A method as claimed in claim 1, wherein the percentage growth inhibition of leukemic cells with increase in the concentration and time duration of exposure to CA and PCQ.

* * * * *